United States Patent
Mercurio et al.

(10) Patent No.: US 8,084,027 B2
(45) Date of Patent: Dec. 27, 2011

(54) COMBINATIONS COMPRISING A CDK INHIBITOR AND A GROWTH FACTOR ANTIBODY OR ANTI-MITOTIC

(75) Inventors: Ciro Mercurio, Legnano (IT); Enrico Pesenti, Parabiago (IT); Maria Grazia Porro, Basel (IT); Paolo Pevarello, Madrid (ES)

(73) Assignee: Nerviano Medical Sciences S.r.l., Nerviano (IT)

( * ) Notice: Subject to any disclaimer, the term of this patent is extended or adjusted under 35 U.S.C. 154(b) by 205 days.

(21) Appl. No.: 12/278,530

(22) PCT Filed: Feb. 2, 2007

(86) PCT No.: PCT/EP2007/051020
§ 371 (c)(1),
(2), (4) Date: Aug. 6, 2008

(87) PCT Pub. No.: WO2007/090794
PCT Pub. Date: Aug. 16, 2007

(65) Prior Publication Data
US 2009/0017025 A1   Jan. 15, 2009

(30) Foreign Application Priority Data
Feb. 10, 2006 (EP) .................................. 06101523

(51) Int. Cl.
*A61K 39/395* (2006.01)
(52) U.S. Cl. ............... 424/133.1; 530/387.1; 530/387.7; 530/387.3; 424/138.1
(58) Field of Classification Search ........................ None
See application file for complete search history.

(56) References Cited

U.S. PATENT DOCUMENTS

| 7,537,762 B2 * | 5/2009 | North et al. ................. 424/146.1 |
| 7,560,111 B2 * | 7/2009 | Kao et al. ..................... 424/138.1 |
| 2005/0239820 A1 * | 10/2005 | Borzilleri et al. ............. 514/300 |

FOREIGN PATENT DOCUMENTS

| EP | 1 568 368 A1 | 8/2005 |
| WO | WO 2004/041268 A1 | 5/2004 |
| WO | WO 2004/104007 A1 | 12/2004 |
| WO | 2007/059099 | * 5/2007 |

OTHER PUBLICATIONS

Wiesenthal (http://weisenthal.org/feedback. html, Feb. 4, 2002).*
Tallarida (Drug Synergism and Dose-effect Analysis, Chapman & Hall/CRC, Boca Raton, 2000, pp. 1-13).*
Berenbaum ("Synergy, additivism and antagonism in immunosuppression," Clin exp Immunol 28:1-18, 1977).*
Shapiro G.I., "Preclinical and Clinical Development of the Cyclin-Dependent Kinase Inhibitor Flavopiridol", *Clinical Cancer Research* 10(12, pt. 2):4270s-4275s (2004).
Senderowicz A.M., "Small-Molecule Cyclin-Dependent Kinase Modulators", *Oncogene* 22(42):6609-6620 (2003).

* cited by examiner

*Primary Examiner* — Sheela J Huff
(74) *Attorney, Agent, or Firm* — Scully, Scott, Murphy & Presser, P.C.

(57) ABSTRACT

The present invention provides a combination comprising a compound A of formula (I) as set forth in the specification or a pharmaceutically acceptable salt thereof, and an antibody inhibiting a growth factor or its receptor and/or an antimitotic agent or a derivative or prodrug thereof, useful in the treatment of tumors. The chemical name of compound A is 8-[4-(4-methyl-piperazin-1-yl)-phenylamino]-1,4,4-trimethyl-4,5-dihydro-1H-pyrazolo[4,3-h]quinazoline-3-carboxylic acid methylamide.

25 Claims, No Drawings

COMBINATIONS COMPRISING A CDK INHIBITOR AND A GROWTH FACTOR ANTIBODY OR ANTI-MITOTIC

TECHNICAL FIELD

The present invention relates in general to the field of cancer treatment and, more particularly, provides an antitumor composition comprising a cdks inhibitor and an antibody inhibiting a growth factor and/or an anti-mitotic compound having a synergistic anti-neoplastic effect.

BACKGROUND ART

It is well known that progression through the cell cycle is governed by a series of checkpoint controls, otherwise referred to as restriction points, which are regulated by a family of enzymes known as the cyclin-dependent kinases (cdks). In turn, the cdks themselves are regulated at many levels such as, for instance, binding to cyclins.

The coordinated activation and inactivation of different cyclin/cdk complexes is necessary for normal progression through the cell cycle. Both the critical G1-S and G2-M transitions are controlled by the activation of different cyclin/cdk activities. In G1, both cyclin D/cdk4 and cyclin E/cdk2 are thought to mediate the onset of S-phase. Progression through S-phase requires the activity of cyclin A/cdk2 whereas the activation of cyclin A/cdc2 (cdk1) and cyclin B/cdc2 are required for the onset of mitosis. For a general reference to cyclins and cyclin-dependent kinases see, for instance, Kevin R. Webster et al, in Exp. Opin. Invest. Drugs, 1998, Vol. 7(6), 865-887.

Checkpoint controls are defective in tumor cells due, in part, to disregulation of cdk activity. For example, altered expression of cyclin E and cdks has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

PCT/WO 2003039536 A (YALE UNIVERSITY) May 15, 2003 and PCT/WO 2004041268 A (CYCLACEL LIMITED) May 21, 2004 relate to the combinations of a taxane like docetaxel or paclitaxel and roscovitine, a protein kinase inhibitor. PCT/WO 2005094830 A (PFIZER INC) Oct. 13, 2005 describes combinations of signal transduction inhibitors such as cdks inhibitors.

There is a continuous need of combination of known anti-cancer drugs in order to optimise the therapeutic treatment.

Some pyrazoloquinazolines have been demonstrated to be potent inhibitors of cyclin dependent kinase enzymes, particularly Cdk2. One of these compounds is currently in development as an anti-cancer agent. Cdks inhibitors are understood to block passage of cells from the G2/M phase of the cell cycle.

The present invention provides new combinations of a Cdks inhibitor with known pharmaceutical agents that are particularly suitable for the treatment of proliferative disorders, especially cancer. More specifically, the combinations of the present invention are very useful in therapy as antitumor agents and lack, in terms of both toxicity and side effects, the drawbacks associated with currently available antitumor drugs.

DISCLOSURE OF THE INVENTION

It is an object of the invention to provide, in a first aspect, a combination comprising a compound A having the following formula (I):

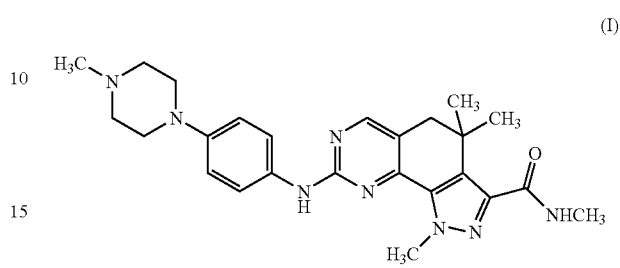

or a pharmaceutically acceptable salt thereof and
an antibody inhibiting a growth factor or its receptor and/or an anti-mitotic agent or a derivative or prodrug thereof.

Another aspect provides a pharmaceutical composition comprising a combination according the invention admixed with a pharmaceutically acceptable carrier, diluent or excipient.

A further aspect relates to the use of a combination according the invention in the preparation of a medicament for treating a proliferative disorder. A still further aspect relates to a pharmaceutical product comprising a compound A as defined above and
an antibody inhibiting a growth factor or its receptor and/or an antimitotic agent, or a derivative or prodrug thereof, as a combined preparation for simultaneous, sequential or separate use in therapy. Another aspect relates to a method of treating a proliferative disorder, said method comprising simultaneously, sequentially or separately administering a compound A as defined above and an antibody inhibiting a growth factor or its receptor and/or an antimitotic agent, or a derivative or prodrug thereof, to a subject.

A still further aspect relates to the use of a compound A as defined above in the preparation of a medicament for the treatment of a proliferative disorder, wherein said treatment comprises simultaneously, sequentially or separately administering a compound A as defined above and an antibody inhibiting a growth factor or its receptor and/or an antimitotic agent, or a derivative or prodrug thereof, to a subject.

Another aspect relates to the use of a compound A as defined above and an antibody inhibiting a growth factor or its receptor and/or an antimitotic agent, or a derivative or prodrug thereof, in the preparation of a medicament for treating a proliferative disorder.

In the present description, unless otherwise specified, the compound A is 8-[4-(4-methyl-piperazin-1-yl)-phenylamino]-1,4,4-trimethyl-4,5-dihydro-1H-pyrazolo[4,3-h]quinazoline-3-carboxylic acid methylamide. It can be prepared as described in PCT/WO 2004104007 A (PHARMACIA ITALIA SPA) Dec. 2, 2004, and is endowed with protein kinase inhibitory activity and is thus useful in therapy as antitumor agent. In particular, the preferred preparation of the compound A is that described in example 58 of the above mentioned International Patent Application.

Pharmaceutically acceptable salts of the compound A include the acid addition salts with inorganic or organic acids, e.g., nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid and the like.

According to a preferred embodiment of the invention, the antibody inhibiting growth factor or its receptor is selected from bevacizumab (antibody to vascular endothelial growth factor), cetuximab, panitumumab, matuzumab, nimotuzumab (antibodies to epidermal growth factor receptor), trastuzumab and pertuzumab (antibodies to ErbB2).

According to a more preferred embodiment of the invention, the antibody inhibiting growth factor or its receptor is bevacizumab.

An anti-mitotic agent is for example an epothilone or a taxane.

Epothilones bind to and stabilize microtubules, and have a broad range of antitumor activity at doses and schedules associated with tolerable side effects, see Journal of Clinical Oncology, Vol 22, No 10 (May 15), 2004: pp. 2015-2025. The main representative epothilones are ixabepilone, BMS-310705, EPO906, and KOS-862.

Taxanes are one of the most powerful classes of compounds among all chemotherapeutic drugs, exhibiting a wide range of activity. The main representative taxanes are paclitaxel and docetaxel. (See for example the review: Cancer, Principles and Practice of Oncology, Lippincott-Raven Ed. (1997), 467-483). Randomised clinical trials evaluating docetaxel and paclitaxel in the first-line treatment setting for metastatic breast, lung, ovarian, and digestive cancers, as well as in the adjuvant setting for breast cancer, have confirmed that taxanes are leading contributors in the armamentarium of cancer treatments; see for example the review: "Docetaxel for treatment of solid tumours: a systematic review of clinical data", Lancet Oncology (2005).

Taxanes have a peculiar mechanism of action: namely hyperstabilisation of microtubules. In details, taxanes target the β subunit of the tubulin heterodimer, the key component of cellular microtubules. This mechanism of action is associated to cell-cycle arrest and apoptosis. The action and anticancer activity of paclitaxel and docetaxel is similar but at the same time, key differences exist, and lack of cross-resistance between taxanes is evident clinically. Docetaxel exhibits greater affinity to β-tubulin, targeting centrosome organization and acting on cells in three phases of the cell cycle (S/G$_2$/M), whereas paclitaxel causes cell damage by affecting the mitotic spindle in the G$_2$ and M phases of the cell cycle.

Therefore, according to the present invention, preferably an anti-mitotic agent is a taxane, more preferably docetaxel or paclitaxel.

In the present invention, the compound A as defined above, or a pharmaceutically acceptable salt thereof and
   an antibody inhibiting a growth factor or its receptor and/or
   an anti-mitotic agent or a derivative or prodrug thereof, are
      in amounts effective to produce a synergic anti-neoplastic effect.

The present invention also provides a method for lowering the side effects caused by anti-neoplastic therapy with an anti-neoplastic agent in mammals, including humans, in need thereof, the method comprising administering to said mammal a combination preparation comprising the compound A as defined above and an anti-mitotic compound and/or an antibody inhibiting growth factors or their receptors as defined above, in amounts effective to produce a synergic anti-neoplastic effect.

By the term "a synergic anti-neoplastic effect" as used herein is meant the inhibition of the growth tumor, preferably the complete regression of the tumor, by administering an effective amount of the combination of a the compound A as defined above and an anti-mitotic compound and/or an antibody inhibiting growth factors or their receptors to mammals, including human.

By the term "administered "or" administering" as used herein is meant parenteral and/or oral administration. By "parenteral" is meant intravenous, subcutaneous and intramuscular administration. In the method of the subject invention, the compound A as defined above may be administered simultaneously with the compound with anti-mitotic activity, and/or a an antibody inhibiting growth factors or their receptors, or the compounds may be administered sequentially, in either order. It will be appreciated that the actual preferred method and order of administration will vary according to, inter alia, the particular formulation of the compound A being utilized, the particular formulation of the anti-mitotic compound, such as one of taxane analog class and of an antibody inhibiting growth factor or its receptors being utilized, the particular tumor model being treated, and the particular host being treated.

In the method of the subject invention, for the administration of the compound A, the course of therapy generally employed is in the range from 5 mg/m$^2$ to 1.5 g/m$^2$ of body surface area. More preferably, the course therapy employed is from about 50 mg/m$^2$ to about 500 mg/m$^2$ of body surface area.

The compound A can be administered in a variety of dosage forms, e.g., orally, in the form of tablets, capsules, sugar or film coated tablets, liquid solutions or suspensions; rectally in the form of suppositories; parenterally, e.g., intramuscularly, or through intravenous and/or intrathecal and/or intraspinal injection or infusion.

In the method of the subject invention, for the administration of the anti-mitotic compounds, preferably docetaxel, the course of therapy generally employed is from about 50 mg/m$^2$ to 100 mg/m$^2$ every three weeks or from 30 mg/m$^2$ weekly.

For the administration of an antibody inhibiting a growth factor, the course of therapy generally employed may be from 0.1 mg/kg to 100 mg/kg. More preferably the course of therapy employed is from 1 mg/kg to 20 mg/kg.

The anti-neoplastic therapy of the present invention is in particular suitable for treating all form of cancer including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; haematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; haematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

As stated above, the effect of the compound A and an anti-mitotic agent or a derivative or prodrug thereof, and/or an antibody inhibiting growth factors or their receptors is significantly increased without a parallel increased toxicity. In other words, the combined therapy of the present invention enhances the antitumoral effects of the compound A and/or of the anti-mitotic compound and/or of an antibody inhibiting growth factors or their receptors and thus yields the most effective and less toxic treatment for tumors.

Pharmaceutical compositions according to the invention are useful in anticancer therapy.

The present invention further provides a commercial kit comprising, in a suitable container mean, a compound A as defined above, and an anti-mitotic agent or a derivative or prodrug thereof.

It is also provided a commercial kit comprising, in a suitable container mean, a compound A as defined above and an antibody inhibiting growth factor or its receptor. In a kit according to the invention a compound A, as defined above, and an antibody inhibiting growth factor or its receptor and/or an anti-mitotic agent or a derivative or prodrug thereof are present within a single container mean or within distinct container means.

Another embodiment of the present invention is a commercial kit comprising a pharmaceutical composition or product as described above.

Kits according to the invention are intended for simultaneous, separate or sequential use in antitumor therapy.

Kits according to the invention are intended for use in anticancer therapy.

Due to the key role of cdks in the regulation of cellular proliferation, the combinations of the present invention are also useful in the treatment of a variety of cell proliferative disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

The combinations of this invention, as modulators of apoptosis, may also be useful in the treatment of cancer, viral infections, prevention of AIDS development in HIV-infected individuals, autoimmune diseases and neurodegenerative disorders.

The activities of the combination of the present invention are shown for instance by the following in vivo tests, which are intended to illustrate but not to limit the present invention.

In vivo antitumor efficacy using the monoclonal antibody

Balb, Nu\Nu male mice, from Harlan (Italy), were maintained in cages with paper filter cover, food and bedding sterilized and water acidified. $2.5 \times 10^6$ DU145 prostate carcinoma cells (from the American Type Culture Collection) were injected subcutaneously in athymic mice. This tumor model was selected because it was previously demonstrated that Bevacizumab inhibits angiogenesis and growth of the model in vivo (see for reference The Prostate 36: 1-10, 1998). The treatment started 6 days later tumor cell injection when tumors were palpable. Bevacizumab was prepared immediately before treatment, while COMPOUND A was prepared every 3 days, on the basis of known stability of the compound.

COMPOUND A was administered by oral route in a volume of 10 ml/kg at the dose of 40 mg/kg twice a day (BID) for 12 days (days 6 to 17). Bevacizumab was administered intraperitoneally in a volume of 10 ml/kg at the dose of 20 mg/kg on days 6, 10, 14, 18 from the days of tumor cells injection. When combined, COMPOUND A was administered in the interval between the bevacizumab treatments at days 7, 8, 9, 11, 12, 13, 15, 16, 17, 19, 20 and 21. Tumor growth and body weight were measured every 3 days. Tumor growth was assessed by caliper. The two diameters were recorded and the tumor weight was calculated according to the following formula: length (mm)×width$^2$/2. The effect of the antitumor treatment was evaluated as the delay in the onset of an exponential growth of the tumor (see for references, Anticancer drugs 7:437-60, 1996). This delay (T-C value) was defined as the difference of time (in days) required for the treatment group (T) and the control group (C) tumors to reach a predetermined size (1 g). Toxicity was evaluated on the basis of body weigh reduction. The results were reported in table below. COMPOUND A combined with bevacizumab produced a clear synergic effect: The T-C observed when COMPOUND A was combined with bevacizumab was superior to the expected by the simple addition of T-C obtained by the single treatments. No toxicity was observed in any of the treatment group.

TABLE 1

| Treatment | Time to reach 1 g (days) | T-C (days) | Toxicity |
|---|---|---|---|
| COMPOUND A 40 mg/kg* | 32.38 ± 2.7 | 16.88 | 0/8 |
| Bevacizumab 20 mg/kg** | 27.93 ± 3.44 | 12.43 | 0/8 |
| Bevacizumab 20 mg/kg + COMPOUND A 40 mg/kg*** | 46.75 ± 5.4 | 31.25 | 0/8 |

*Treatments made orally twice at days 6, 7, 8, 9, 10, 11, 12, 13, 14, 15, 16 and 17
**Treatments made intraperitoneally at days 6, 10, 14 and 18
***Days 6, 10, 14 and 18 bevacizumab treatments; days 7, 8, 9, 11, 12, 13, 15, 16, 17, 19, 20 and 21 COMPOUND A treatments In vivo antitumor efficacy using docetaxel Balb, Nu\Nu male mice, from Harlan (Italy), were maintained in cages with paper filter cover, food and bedding sterilized and water acidified. $2.5 \times 10^6$ DU145 prostate carcinoma cells (from the American Type Culture Collection) were injected subcutaneously in athymic mice. This tumor model was selected because it was previously demonstrated that docetaxel inhibits growth of the model in vivo (see for reference: Cancer Res. 2004 Oct. 15, (64): 7426-31) and also on the basis of use of this drug in prostate cancer (see for references, Approval summary: docetaxel in combination with prednisone for the treatment of androgen-independent hormone-refractory prostate cancer, Clin. Cancer Res. 2004 Dec. 15; 10(24): 8147-51).

The treatment started 10 days later tumor cells injection when tumors were palpable. Docetaxel was prepared immediately before treatment, while COMPOUND A was prepared every 3 days, on the basis of known stability of the compound.

COMPOUND A was administered by oral route in a volume of 10 ml/kg at the doses of 40 mg/kg twice a day (BID) for 9 days (days 10 to 18). Docetaxel was administered by intravenous route in a volume of 10 ml/kg at the dose of 10 mg/kg on days 10, 14, 18 from the days of cell injection. When combined, COMPOUND A was administered in the interval between the docetaxel treatments at days 11, 12, 13, 15, 16, 17, 19, 20 and 21. Tumor growth and body weight were measured every 3 days. Tumor growth was assessed by caliper. The two diameters were recorded and the tumor weight was calculated according to the following formula: length (mm)×width$^2$/2. The effect of the antitumor treatment was evaluated as the delay in the onset of an exponential growth of the tumor (see for references, Anticancer drugs 7:437-60, 1996). This delay (T-C value) was defined as the difference of time (in days) required for the treatment group (T) and the control group (C) tumors to reach a predetermined size (1 g). Toxicity was evaluated on the basis of body weight reduction. The results were reported in table below. COMPOUND A combined with docetaxel produced a clear synergistic effect: The T-C observed when COMPOUND A was combined with docetaxel was superior (20.37 days) to the expected by simple addition of T-C (15.27) obtained by the single treatments. No toxicity was observed in any of the treatment groups.

TABLE 2

| Treatment | Time to reach 1 g (days) | T-C (days) | Toxicity |
|---|---|---|---|
| Compound A 40 mg/kg* | 27.4 ± 2.7 | 10.21 | 0/8 |
| Docetaxel 10 mg/kg** | 22.25 ± 2.98 | 5.05 | 0/8 |
| Docetaxel 10 mg/kg + Compound A 40 mg/kg*** | 37.5 ± 2.98 | 20.37 | 0/8 |

*Treatments made orally twice at days 10, 11, 12, 13, 14, 15, 16, 17, 18.
**Treatments made by intravenous route at days 10, 14, 17
***Days 10, 14, 18 docetaxel treatments, days 11, 12, 13, 15, 16, 17, 19, 20 and 21 Compound A treatments

The invention claimed is:

1. A combination comprising a compound A of formula (I):

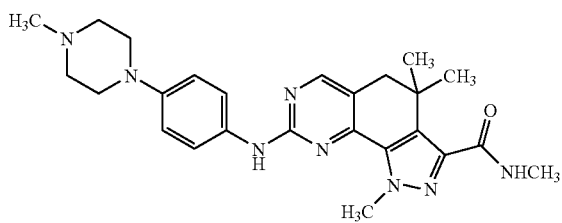

(I)

or a pharmaceutically acceptable salt thereof, and bevacizumab.

2. A combination comprising a compound A of formula (I):

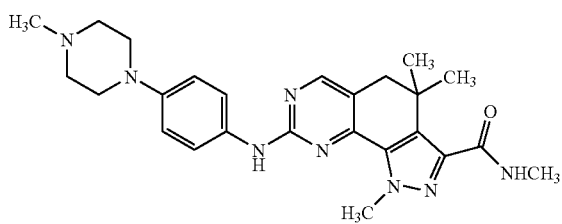

(I)

or a pharmaceutically acceptable salt thereof, and a taxane.

3. A combination comprising a compound A of formula (I):

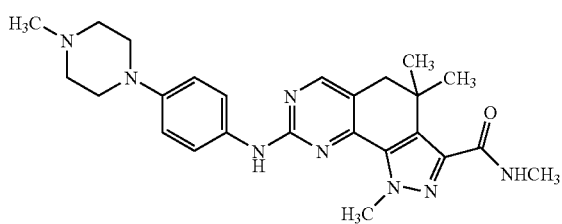

(I)

or a pharmaceutically acceptable salt thereof, and bevacizumab, and a taxane.

4. The compound A according to claim 1, 2 or 3 wherein said compound A is 8-[4-(4-methyl-piperazin-1-yl)-phenylamino]-1,4,4-trimethyl-4,5-dihydro-1H-pyrazolo[4,3-h]quinazoline-3-carboxylic acid methylamide.

5. The taxane according to claim 2 wherein said taxane is paclitaxel or docetaxel.

6. A pharmaceutical composition comprising the combination according to claim 1 and a pharmaceutically acceptable carrier, diluent or excipient.

7. A pharmaceutical composition comprising the combination according to claim 2 and a pharmaceutically acceptable carrier, diluent or excipient.

8. A pharmaceutical composition comprising the combination according to claim 3 and a pharmaceutically acceptable carrier, diluent or excipient.

9. A pharmaceutical product comprising compound A according to claim 4 and an antibody inhibiting a growth factor or a receptor of the growth factor, as a combined preparation for simultaneous, sequential or separate use in therapy.

10. A pharmaceutical product comprising compound A according to claim 4 and an anti-mitotic agent or a derivative or prodrug thereof, as a combined preparation for simultaneous, sequential or separate use in therapy.

11. A pharmaceutical product comprising compound A according to claim 4 and an antibody inhibiting a growth factor or a receptor of the growth factor, and an anti-mitotic agent or a derivative or prodrug thereof, as a combined preparation for simultaneous, sequential or separate use in therapy.

12. A method of treating a proliferative disorder comprising simultaneously, sequentially or separately administering components of the combination according to claim 1 to a subject.

13. A method of treating a proliferative disorder comprising simultaneously, sequentially or separately administering components of the combination according to claim 2 to a subject.

14. A method of treating a proliferative disorder comprising simultaneously, sequentially or separately administering components of the combination according to claim 3 to a subject.

15. A method for lowering the side effects caused by anti-neoplastic therapy with an anti-neoplastic agent in mammals, in need thereof, said method comprising administering to said mammal the combination according to claim 1 in amounts effective to produce an anti-neoplastic effect.

16. A method for lowering the side effects caused by anti-neoplastic therapy with an anti-neoplastic agent in mammals, in need thereof, said method comprising administering to said mammal the combination according to claim 2 in amounts effective to produce an anti-neoplastic effect.

17. A method for lowering the side effects caused by anti-neoplastic therapy with an anti-neoplastic agent in mammals, in need thereof, said method comprising administering to said mammal the combination according to claim 3 in amounts effective to produce an anti-neoplastic effect.

18. The method of lowering the side effects according to claim 15 wherein the mammals are humans.

19. A commercial kit comprising, in a suitable container means, the combination according to claim 1.

20. A commercial kit comprising, in a suitable container means, the combination according to claim 2.

21. A commercial kit comprising, in a suitable container means, the combination according to claim 3.

22. A commercial kit comprising the pharmaceutical composition according to claim 6.

23. A commercial kit comprising the pharmaceutical product according to claim 9.

24. A commercial kit comprising the pharmaceutical product according to claim 10.

25. A commercial kit comprising the pharmaceutical product according to claim 11.

\* \* \* \* \*